US008076383B2

(12) United States Patent
Konishi et al.

(10) Patent No.: US 8,076,383 B2
(45) Date of Patent: Dec. 13, 2011

(54) POROUS RESIN PARTICLE HAVING HYDROXY GROUP OR PRIMARY AMINO GROUP AND PRODUCTION METHOD THEREOF

(75) Inventors: Tatsuya Konishi, Osaka (JP); Kenjiro Mori, Osaka (JP)

(73) Assignee: Nitto Denko Corporation, Osaka (JP)

( * ) Notice: Subject to any disclaimer, the term of this patent is extended or adjusted under 35 U.S.C. 154(b) by 332 days.

(21) Appl. No.: 12/265,270

(22) Filed: Nov. 5, 2008

(65) Prior Publication Data

US 2009/0124714 A1   May 14, 2009

(30) Foreign Application Priority Data

Nov. 5, 2007 (JP) .............................. P. 2007-286836

(51) Int. Cl.
*C08J 9/28* (2006.01)
(52) U.S. Cl. ......... 521/61; 428/402.22; 521/62; 521/63; 521/64; 521/139; 521/140; 521/146; 521/147; 524/457; 524/475; 524/555; 524/800; 524/848
(58) Field of Classification Search .................... 521/61, 521/62, 63, 64, 139, 140, 146, 147; 428/402.22; 524/457, 459, 475, 555, 800, 848
See application file for complete search history.

(56) References Cited

U.S. PATENT DOCUMENTS

| 3,586,644 | A | | 6/1971 | De Jong | |
|---|---|---|---|---|---|
| 4,098,727 | A | | 7/1978 | Haag et al. | |
| 4,908,405 | A | | 3/1990 | Bayer et al. | |
| 4,950,408 | A | | 8/1990 | Duisters et al. | |
| 5,227,463 | A | | 7/1993 | Arsenault | |
| 5,248,435 | A | * | 9/1993 | Morita et al. ................. | 210/681 |
| 6,147,159 | A | * | 11/2000 | Hu et al. ......................... | 506/32 |
| 2005/0031871 | A1 | * | 2/2005 | Kinsho et al. ................. | 428/402 |
| 2007/0066761 | A1 | * | 3/2007 | Deetz et al. .................... | 525/309 |
| 2008/0039578 | A1 | * | 2/2008 | Fonnum et al. ............... | 524/555 |

FOREIGN PATENT DOCUMENTS

| EP | 0788839 A1 | 8/1997 |
|---|---|---|
| EP | 1109069 A2 | 6/2001 |
| EP | 1595895 A1 | 11/2005 |
| JP | 2004-339304 A | 12/2004 |

OTHER PUBLICATIONS

Extended European Search Report dated Feb. 19, 2009.
Office Action dated Jul. 20, 2011 from the State Intellectual Property Office of the People's Republic of China in counterpart Chinese application No. 200810174429.7.

* cited by examiner

*Primary Examiner* — John Cooney
(74) *Attorney, Agent, or Firm* — Sughrue Mion, PLLC

(57) ABSTRACT

The present invention relates to a method for producing a porous resin particle having a functional group X, the method including: dissolving a radical polymerizable aromatic monovinyl monomer and a radical polymerizable aromatic divinyl monomer together with a polymerization initiator in an organic solvent to prepare a monomer solution, dispersing the monomer solution in water in the presence of a dispersion stabilizer to obtain a suspension polymerization reaction mixture, and performing a suspension copolymerization while adding, when 0 to 80% of the entire polymerization time of the suspension copolymerization is passed, a mercapto compound represented by the formula (I):

$$HS-R-X \qquad (I)$$

in which R represents an alkylene group having a carbon number of 2 to 12, and the functional group X represents a functional group selected from a hydroxy group and a primary amino group, to the suspension polymerization reaction mixture; and the porous resin particle obtained by the method.

3 Claims, No Drawings

POROUS RESIN PARTICLE HAVING HYDROXY GROUP OR PRIMARY AMINO GROUP AND PRODUCTION METHOD THEREOF

FIELD OF THE INVENTION

The present invention relates to a porous resin particle having a hydroxy group or a primary amino group, which can be suitably used as a support for solid phase synthesis, and a production method thereof.

BACKGROUND OF THE INVENTION

A styrene-divinylbenzene porous resin particle has been widely used in the fields of ion exchange resin, adsorbent, packing agent for liquid chromatography, support for solid phase synthesis, and the like. The porous resin particle used for such applications has some functional group in many cases and is usually produced though a plurality of steps. For example, there are a method including preparing a styrene-divinylbenzene porous resin particle by suspension polymerization, collecting the obtained resin particle, and reacting various substances with the residual vinyl group to introduce a functional group into the resin (see, for example, Patent Documents 1 to 3). According to such a method, however, two steps, that is, polymerization step and functionalizing step, are necessary.

Furthermore, there is also a method of grafting a polyethylene glycol to a polychloromethylstyrene resin to produce a porous resin particle having a hydroxy group (see, Patent Document 4), but this method also requires two steps, that is, polymerization step and grafting step.

As another problem, the styrene-divinylbenzene porous resin particle is well swelled in a nonpolar solvent such as toluene and dichloromethane but is difficult to swell in a polar solvent such as acetonitrile and ethanol. Particularly, in a solid phase synthesis reaction using a styrene-divinylbenzene porous resin particle as the support for solid phase synthesis, for obtaining the objective reaction product in a larger amount, the porous resin particle is preferably swelled to a certain extent in an organic solvent. However, in the case where a chemical reaction is performed by sequentially using a plurality of organic solvents and where the swelling degree of the resin differs among the organic solvents, when, for example, a column-like reaction vessel having a given volume is used, the pressure fluctuates in the vessel and this may give rise to variation in the yield of the objective synthesis reaction.

Patent Document 1: U.S. Pat. No. 3,586,644
Patent Document 2: U.S. Pat. No. 4,098,727
Patent Document 3: U.S. Pat. No. 4,950,408
Patent Document 4: U.S. Pat. No. 4,908,405

SUMMARY OF THE INVENTION

Under these circumstances, an object of the present invention is to provide a porous resin particle which does not greatly vary in the swelling degree depending on the kind of the organic solvent and a production method thereof.

Accordingly, the present invention provides the following items 1 to 10.

1. A method for producing a porous resin particle having a functional group X, the method comprising:

dissolving a radical polymerizable aromatic monovinyl monomer and a radical polymerizable aromatic divinyl monomer together with a polymerization initiator in an organic solvent to prepare a monomer solution;

dispersing the monomer solution in water in the presence of a dispersion stabilizer to obtain a suspension polymerization reaction mixture; and performing a suspension copolymerization while adding, when 0 to 80% of the entire polymerization time of the suspension copolymerization is passed, a mercapto compound represented by the formula (I):

$$\text{HS—R—X} \qquad \text{(I)}$$

wherein R represents an alkylene group having a carbon number of 2 to 12, and the functional group X represents a functional group selected from a hydroxy group and a primary amino group, to the suspension polymerization reaction mixture.

2. The method for producing a porous resin particle having a functional group X according to item 1, wherein the proportion of the aromatic divinyl monomer is 6 to 80 wt % based on the total amount of the aromatic monovinyl monomer and the aromatic divinyl monomer, and the mercapto compound is added to the suspension polymerization reaction mixture in an amount of 1 to 20 wt % based on the total amount of the aromatic monovinyl monomer and the aromatic divinyl monomer.

3. The method for producing a porous resin particle having a functional group X according to item 1 or 2, wherein the aromatic monovinyl monomer is styrene.

4. The method for producing a porous resin particle having a functional group X according to item 1, wherein the mercapto compound is added to the suspension polymerization reaction mixture when 5 to 60% of the entire polymerization time is passed.

5. A porous resin particle having a functional group X, which is obtained by:

dissolving a radical polymerizable aromatic monovinyl monomer and a radical polymerizable aromatic divinyl monomer together with a polymerization initiator in an organic solvent to prepare a monomer solution;

dispersing the monomer solution in water in the presence of a dispersion stabilizer to obtain a suspension polymerization reaction mixture; and performing a suspension copolymerization while adding, when 0 to 80% of the entire polymerization time of the suspension copolymerization is passed, a mercapto compound represented by the formula (I):

$$\text{HS—R—X} \qquad \text{(I)}$$

wherein R represents an alkylene group having a carbon number of 2 to 12, and the functional group X represents a functional group selected from a hydroxy group and a primary amino group, to the suspension polymerization reaction mixture.

6. The porous resin particle having a functional group X according to item 5, wherein the proportion of the aromatic divinyl monomer is 6 to 80 wt % based on the total amount of the aromatic monovinyl monomer and the aromatic divinyl monomer, and the mercapto compound is used in an amount of 1 to 20 wt % based on the total amount of the aromatic monovinyl monomer and the aromatic divinyl monomer.

7. The porous resin particle having a functional group X according to item 5 or 6, wherein the aromatic monovinyl monomer is styrene.

8. The porous resin particle having a functional group X according to any one of items 5 to 7, which has a hydroxy group or a primary amino group in an amount of 10 to 1,500 µmol/g.

9. A support for solid phase synthesis, comprising the porous resin particle having a functional group X according to any one of items 5 to 8.

10. The support for solid phase synthesis according to item 9, which is for the synthesis of oligonucleotide or a derivative thereof.

According to the method of the present invention, unlike conventional methods, a porous resin particle having a hydroxy group or a primary amino group can be obtained through a single step without the necessity of a functionalizing step after the polymerization step.

Furthermore, since the porous resin particle obtained by the method of the present invention does not greatly vary in the swelling degree among various organic solvents, when a chemical reaction is performed sequentially in various organic solvents by using the porous resin particle as the support for solid phase synthesis, the synthesis reaction on the support can be efficiently performed.

DETAILED DESCRIPTION OF THE INVENTION

The method for producing a porous resin particle having a hydroxy group or a primary amino group of the present invention includes: dissolving a radical polymerizable aromatic monovinyl monomer and a radical polymerizable aromatic divinyl monomer together with a polymerization initiator in an organic solvent to prepare a monomer solution; dispersing the monomer solution in water in the presence of a dispersion stabilizer to obtain a suspension polymerization reaction mixture; and performing suspension copolymerization while adding, when 0 to 80% of the entire polymerization time of the suspension copolymerization is passed, a mercapto compound represented by the formula (I):

$$HS-R-X \qquad (I)$$

(wherein R represents an alkylene group having a carbon number of 2 to 12, and the functional group X represents a functional group selected from a hydroxy group and a primary amino group) to the suspension polymerization reaction mixture.

In the present invention, examples of the aromatic monovinyl monomer include styrene, a nucleus alkyl-substituted styrene such as o-methylstyrene, m-methylstyrene, p-methylstyrene, 2,4-dimethylstyrene, 2,5-dimethylstyrene, 3-ethylstyrene, 4-ethylstyrene and p-tert-butylstyrene, an α-alkyl-substituted styrene such as α-methylstyrene and α-methyl-p-methylstyrene, and p-acetoxystyrene. One of these aromatic monovinyl monomers may be used alone, or two or more thereof may be used in combination. According to the present invention, styrene is preferred among all.

In the present invention, the aromatic divinyl monomer is a polyfunctional compound having two vinyl groups on the aromatic ring and is used as a crosslinking agent. That is, it forms a copolymer having a crosslinked structure together with the aromatic monovinyl monomer. Usually, divinylbenzene is preferably used as the aromatic divinyl monomer.

In the present invention, the aromatic divinyl monomer is usually used in an amount of 6 to 80 wt %, preferably from 8 to 70 wt %, and most preferably from 15 to 65 wt %, based on the total amount of the aromatic monovinyl monomer and the aromatic divinyl monomer. If the proportion of the aromatic divinyl monomer is less than 6 wt %, the porous resin particle to be obtained is insufficient in the solvent resistance or thermal stability and when used as a support for solid phase synthesis, the desired effects can be hardly expected, whereas if it exceeds 80 wt %, only a porous resin particle having poor swellability can be obtained due to overcrosslinking and when used as a support for solid phase synthesis, sufficiently high reaction efficiency may not be obtained.

According to the present invention, suspension polymerization is performed by dissolving an aromatic monovinyl monomer and an aromatic divinyl monomer together with a polymerization initiator in an organic solvent and dispersing the solution in water, so that phase separation can be effectively caused to occur in the suspension polymerization and in turn, the produced resin particle can be made to have a homogeneous porous structure in the inside thereof.

In the present invention, the organic solvent is not particularly limited so long as it is insoluble in water which is a reaction medium, but examples thereof include an aliphatic hydrocarbon such as hexane, heptane, octane, isooctane, undecane and dodecane, and an aliphatic alcohol such as 2-ethylhexanol, tert-amyl alcohol, nonyl alcohol, 2-octanol, decanol, lauryl alcohol and cyclohexanol. One of these organic solvents may be used alone, or two or more thereof may be used in combination.

The organic solvent is usually used in a range from 0.1 to 2 times, preferably from 0.5 to 1.5 times, in terms of the weight ratio based on the total of the aromatic monovinyl monomer and the aromatic divinyl monomer. If the amount of the organic solvent used exceeds 2 times in terms of the weight ratio based on the total of the aromatic monovinyl monomer and the aromatic divinyl monomer, the resin particle to be formed may not have sufficient strength due to too high porosity and a spherical particle can be hardly formed, whereby when used as a support for solid phase synthesis, the desired effects cannot be obtained. On the other hand, if the amount of the organic solvent used is less than 0.1 times in terms of the weight ratio based on the total of the aromatic monovinyl monomer and the aromatic divinyl monomer, the particle to be formed fails in having a sufficient porosity and when used as an ion exchange resin, a packing material for chromatography, a support for solid phase synthesis, an adsorbent or the like, the desired effects can be hardly exerted.

According to the method of the present invention, the aromatic monovinyl monomer and the aromatic divinyl monomer are dissolved together with a polymerization initiator in an organic solvent to prepare a monomer solution, the monomer solution is dispersed in water in the presence of a dispersion stabilizer to obtain a suspension polymerization reaction mixture, and suspension copolymerization is performed while adding the mercapto compound to the suspension polymerization reaction mixture when 0 to 80% of the entire polymerization time of the suspension copolymerization is passed, whereby a porous resin particle having a hydroxy group or a primary amino group according to the mercapto compound used can be obtained immediately through a single step, that is, only through the suspension polymerization step, without the necessity of performing a functionalizing step subsequently to the suspension polymerization step.

In the present invention, the expression "performing suspension copolymerization while adding a mercapto compound represented by the formula (I) to the suspension polymerization reaction mixture when 0% of the entire polymerization time is passed" means that the mercapto compound is added to the suspension polymerization reaction mixture before or at the initiation of the suspension polymerization.

In particular, according to the present invention, the mercapto compound is preferably added to the suspension polymerization reaction mixture when 5 to 60% of the entire polymerization time is passed, and most preferably when 10 to 50% of the entire polymerization time is passed.

In the present invention, the mercapto compound is a mercaptoalkyl alcohol when the functional group X is a hydroxy group, and is a mercaptoalkylamine when the functional group X is a primary amino group.

Specific examples of the mercaptoalkyl alcohol include mercaptoethanol, 3-mercapto-1-propanol, 1-mercapto-2-propanol, 6-mercaptohexanol, 3-mercapto-1-hexanol, mercaptohexanol, 2-mercaptophenol, 3-mercaptophenol, 4-mercaptophenol and 11-mercapto-1-undecanol.

Specific examples of the mercaptoalkylamine include 2-mercaptoethylamine, 3-mercaptopropylamine, 4-mercaptobutylamine, 2-amino-2-methylpropanethiol, 2-amino-1-methylethanethiol, 2-amino-1,1-dimethylpropanethiol, 3-amino-3-methyl-2-methyl-2-butanethiol, 1-amino-2-hexanethiol, 11-amino-1-undecanethiol and p-aminobenzenethiol.

In the present invention, the mercapto compound represented by the formula (I), that is, the above-described mercaptoalkyl alcohol or mercaptoalkylamine, is usually used in a range of 1 to 20 wt %, preferably from 2 to 15 wt %, and most preferably from 3 to 12 wt %, based on the total amount of the aromatic monovinyl monomer and the aromatic divinyl monomer.

If the amount of the mercapto compound used is less than 1 wt % based on the total amount of the aromatic monovinyl monomer and the aromatic divinyl monomer, a hydroxy group or primary amino group in an amount large enough to enable use as a support for solid phase synthesis cannot be imparted to the porous resin particle to be formed, whereas if the amount of the mercapto compound used exceeds 20 wt %, a chain transfer reaction vigorously occurs in the suspension copolymerization and the polymerization reaction may not proceed.

In the present invention, the dispersion stabilizer used is not particularly limited, and a conventionally known dispersion stabilizer such as hydrophilic protective colloid agent (e.g., polyvinyl alcohol, polyvinylpyrrolidone, polyacrylic acid, gelatin, starch and carboxyl methyl cellulose) and hardly-soluble powder (e.g., calcium carbonate, magnesium carbonate, calcium phosphate, barium sulfate, calcium sulfate and bentonite) may be used. Although not particularly limited, the dispersion stabilizer is usually used in a range of 0.01 to 10 wt % based on the weight of water in the suspension polymerization reaction mixture. If the amount of the dispersion stabilizer used is less than 0.01 wt % based on the weight of water in the suspension polymerization reaction mixture, the dispersion stability of suspension polymerization is impaired and a large amount of an aggregate is produced. On the other hand, if the amount of the dispersion stabilizer used exceeds 10 wt % based on the weight of water in the suspension polymerization reaction mixture, a large amount of a fine particle is produced and filtration after polymerization or removal of the dispersion stabilizer through water washing may become difficult.

Further, the polymerization initiator is not particularly limited and a conventionally known polymerization initiator is appropriately used. For example, a peroxide such as dibenzoyl peroxide, dilauroyl peroxide, distearoyl peroxide, 1,1-di(tert-butylperoxy)-2-methylcyclohexane, 1,1-di(tert-hexylperoxy)-3,3,5-trimethylcyclohexane, 1,1-di(tert-hexylperoxy)cyclohexane, 1,1-di(tert-butylperoxy)cyclohexane, di-tert-hexyl peroxide, tert-butylcumyl peroxide, di-tert-butyl peroxide, 1,1,3,3-tetramethylbutylperoxy-2-ethylhexanoate, tert-hexylperoxy-2-ethylhexanoate, tert-butylperoxy-2-ethylhexanoate and tert-butylperoxyisopropyl monocarbonate, or an azo compound such as 2,2'-azobisisobutyronitrile, 2,2'-azobis-2-methylbutyronitrile and 2,2'-azobis-2,4-dimethylvaleronitrile may be used.

In the method of the present invention, water is used as the reaction medium, and ion exchanged water or pure water is preferred. The suspension polymerization is performed under stirring at a temperature of 60 to 90° C. for 30 minutes to 48 hours in an inert gas stream such as nitrogen.

After the suspension polymerization is thus performed for a predetermined time, the polymerization product is collected by filtration, followed by washing and subsequent drying, whereby the objective porous resin particle can be obtained as a powder. According to the necessity, the powder may be further subjected to a treatment such as classification.

According to the method of the present invention, in this way, a porous resin particle having a hydroxy group or a primary amino group can be obtained immediately through a single step. That is, a functionalizing step for imparting a hydroxy group or a primary amino group to the obtained resin particle is not necessary after the suspension polymerization. Conventionally, in order to obtain a porous resin particle having a hydroxy group, for example, a polymerization step and a functionalizing step are necessary and therefore steps of washing and drying the resin particle are required after the respective steps. On the other hand, according to the method of the present invention, washing and drying may be performed only at once.

The porous resin particle obtained by the method of the present invention does not greatly vary in the swelling degree among various organic solvents and therefore, when this is used as a support for solid phase synthesis and a chemical reaction is performed sequentially in various organic solvents, the synthesis reaction on the support can be efficiently performed. That is, in a series of steps of a chemical synthesis reaction, even in the case that a plurality of organic solvents are exchanged and used, when the porous resin particle of the present invention as a support for solid phase synthesis, a problem such as fluctuation of pressure in a column-like reaction vessel having a given volume can be eliminated by virtue of a small difference in the swelling degree among respective organic solvents.

The porous resin particle obtained by the method of the present invention contains the functional group represented by X, that is, the hydroxy group or primary amino group, in an amount of 10 to 1,500 μmol/g, preferably from 25 to 1,200 μmol/g, and most preferably from 50 to 1,000 μmol/g. If the amount of the functional group is less than 10 μmol/g, when the particle is used as a support for solid phase synthesis, the amount of the synthesis reaction product to be obtained decreases. On the other hand, if the amount of the functional group exceeds 1,500 μmol/g, the distance between adjacent functional groups on the resin particle is insufficient and chemical reactions occurring adjacently to each other are hence readily inhibited with each other, and as a result, when used as a support for solid phase synthesis, the synthesis reaction product to be obtained may be decreased in the purity.

The porous resin particle obtained by the method of the present invention usually has a specific surface area of 0.1 to 500 $m^2/g$, preferably from 10 to 300 $m^2/g$, most preferably from 30 to 200 $m^2/g$. If the specific surface area of the porous resin particle is too small, the chance of the functional group on the surface of the support for solid phase synthesis, which is the reaction site, to contact with a substance participated in the reaction is reduced and in turn, the desired synthesis reaction hardly occurs, resulting in a small amount of synthesis product. On the contrary, if the specific surface area is too large, the void percentage becomes excessively large and the strength of the support itself may decrease to make the handling difficult.

The average pore diameter of pores in the porous resin particle obtained by the method of the present invention is usually from 1 to 300 nm, preferably from 5 to 250 nm, and most preferably from 10 to 200 nm. If the average pore diameter is less than 1 nm, when used as a support for solid phase synthesis, the substance participated in the reaction is not instantly permeated into the inside of the support and the desired synthesis reaction hardly occurs, resulting in a small amount of synthesis product. Further, in the course of separating the synthesis product from the support after the synthesis, the synthesis product inside of the support is difficult to collect to thereby decrease the yield. However, if the average pore diameter exceeds 300 nm, because of the small specific surface area, the chance of the functional group on the surface of the support for solid phase synthesis, which is the reaction site, to contact with a substance participated in the reaction is reduced and the particle is not preferred as a support for solid phase synthesis.

The porous resin particle obtained by the method of the present invention is suitably used as a support for solid phase synthesis, and the target of the solid phase synthesis is not limited and examples thereof include peptide, oligonucleotide, sugar chain, glycopeptide and their derivatives. In particular, the porous resin particle is suitably used for the synthesis of oligonucleotide or a derivative thereof.

The oligonucleotide synthesis using the porous resin particle obtained by the method of the present invention can be performed by a conventionally known method. For example, a linker is bound to the hydroxy group or primary amino group of the porous resin particle, and amidite (nucleoside phosphoramidite) units are bound one by one to give a predetermined base sequence from the terminal of the linker. This synthesis reaction can be performed using an automatic synthesis apparatus. For example, in the apparatus, various organic solvents such as acetonitrile and an amidite solution are sequentially fed to a flow-type reactor packed with a linker-bound porous resin particle and the reaction is repeated. Finally, the linker portion is cut off by hydrolysis or the like, whereby the objective oligonucleotide can be obtained. As for the linker, a conventionally known linker is used. For example, the support for solid phase synthesis containing the porous resin particle of the present invention bound with a nucleoside linker includes a support represented by the following formula:

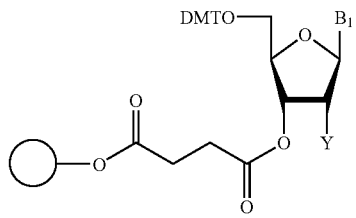

wherein the circle represents the porous resin particle (support for solid phase synthesis) of the present invention, DMT represents a protective dimethoxytrityl group at the 5'-position, $B_1$ represents a base, and Y represents H, F or OH (which may be protected by an appropriate protective group).

EXAMPLES

The present invention is described in greater detail below by referring to Examples, but the present invention is not limited to these Examples.

Example 1

In a 500 mL-volume separable flask equipped with a condenser, a stirrer and a nitrogen inlet tube, 1.97 g of polyvinyl alcohol and 197 g of distilled water were charged and stirred at 200 rpm to dissolve the polyvinyl alcohol in water. Separately, 22.4 g of styrene, 22.4 g of divinylbenzene (purity: 55%, the remaining is almost ethylbenzene), 41.9 g of 2-ethylhexanol, 17.5 g of isooctane and 0.84 g of benzoyl peroxide (25% aqueous product) were mixed and dissolved to prepare a monomer solution. This monomer solution was charged into the separable flask above and after stirring at a stirring rate of 480 rpm in a nitrogen stream at room temperature, polymerization was initiated by raising the temperature to 80° C. When 2 hours was passed after the initiation of polymerization, 2.50 g of mercaptoethanol was added to the suspension polymerization reaction mixture (that is, the suspension polymerization reaction solution), and the polymerization was further continued for 8 hours. After the polymerization, the obtained polymerization product was collected by filtration, then washed with distilled water, acetone and methanol and vacuum-dried to obtain hydroxy group-containing porous resin particle A as powder.

Example 2

Hydroxy group-containing porous resin particle B was obtained as powder in the same manner as in Example 1 except that 2.50 g of mercaptoethanol was added when 4 hours was passed after the initiation of polymerization.

Example 3

Hydroxy group-containing porous resin particle C was obtained as powder in the same manner as in Example 1 except for using 13.5 g of styrene, 31.4 g of divinylbenzene and 1.73 g of mercaptoethanol.

Example 4

Hydroxy group-containing porous resin particle D was obtained as powder in the same manner as in Example 1 except that 13.5 g of styrene and 31.4 g of divinylbenzene were used and 4.50 g of mercaptohexanol was added to the suspension polymerization reaction mixture in place of mercaptoethanol when 4 hours was passed after the initiation of polymerization.

Example 5

Primary amino group-containing porous resin particle E was obtained as powder in the same manner as in Example 1 except that 1.73 g of 2-mercaptoethylamine was used in place of mercaptoethanol.

Comparative Example 1

Suspension Polymerization

In a 500 mL-volume separable flask equipped with a condenser, a stirrer and a nitrogen inlet tube, 2.5 g of polyvinyl alcohol and 250 g of distilled water were charged and stirred at 200 rpm to dissolve the polyvinyl alcohol in water. Separately, 49 g of styrene, 4 g of p-acetoxystyrene, 7 g of divinylbenzene (purity: 55%, the remaining is almost ethylbenzene), 55 g of 2-ethylhexanol, 23 g of isooctane and 1 g of benzoyl peroxide (25% aqueous product) were mixed and dissolved to prepare a monomer solution. This monomer solution was charged into the separable flask above and after stirring at a stirring rate of 400 rpm in a nitrogen stream at room temperature, the temperature was raised to 80° C. Thereafter, the polymerization was continued for 10 hours. After the polymerization, the polymerization product was collected by filtration, then washed with distilled water, acetone and methanol and vacuum-dried to obtain 40 g of a porous resin particle composed of a styrene-acetoxystyrene-divinylbenzene copolymer, as powder.

(Hydrolysis)

In a 500 mL-volume separable flask, 40 g of the powder of styrene-acetoxystyrene-divinylbenzene copolymer above and 250 g of ethanol were charged and stirred at 500 rpm to disperse the copolymer in ethanol. To this liquid dispersion, an aqueous solution obtained by dissolving 2 g of sodium hydroxide in 100 g of distilled water was added. Thereafter, the temperature was raised to 80° C. and the hydrolysis reaction was performed for 24 hours. The reaction solution was neutralized with hydrochloric acid and then subjected to filtration washing by using distilled water and acetone. The resulting liquid dispersion was filtered and then dried under reduced pressure to obtain hydroxy group-containing porous resin particle F as powder.

Test Examples

Porous resin particles A to F obtained in Examples 1 to 5 and Comparative Example 1 were determined for the following physical values. The results are shown in Table 1.

(1) Quantitative Determination of Hydroxy Group

The hydroxy group was quantitatively determined by a titration method according to JIS K 0070.

(2) Quantitative Determination of Primary Amino Group

The nitrogen was quantitatively determined using a total trace nitrogen analyzer (TN-110, manufactured by Mitsubishi Chemical Corp.).

(3) Specific Surface Area and Average Pore Diameter

These were determined by a mercury penetration method. That is, about 0.2 g of the measurement sample was charged into a mercury porosimeter (Pore Mater 60 GT, manufactured by Quantachrome Co.) and from the mercury injection pressure under the conditions of a mercury contact angle of 140° and a mercury surface tension of 480 dyn/cm, the average pore diameter and specific surface area of the measurement sample were determined.

(4) Average Particle Diameter

The median diameter was determined by laser diffraction (light-scattering system)

TABLE 1

|   | Amount of Hydroxyl Group (μmol/g) | Amount of Primary Amino Group (μmol/g) | Specific Surface Area (m²/g) | Average Pore Diameter (nm) | Average Particle Diameter (μm) |
|---|---|---|---|---|---|
| A | 503 | — | 184 | 31 | 85 |
| B | 496 | — | 185 | 39 | 85 |
| C | 698 | — | 190 | 29 | 88 |
| D | 348 | — | 209 | 39 | 87 |
| E | — | 54 | 190 | 39 | 93 |
| F | 416 | — | 145 | 28 | 90 |

(5) Swelling Degree

The apparent volume (that is, dry volume Vd) was measured by placing 1 g of the porous resin particle in a 20 mL-volume graduated cylinder. A large excess of organic solvent was then added to the graduated cylinder, and the porous resin particle was swelled while standing still at room temperature for 24 hours. The thus-swelled porous resin particle was measured for the apparent volume (that is, swollen volume Vs), and Vs/Vd was defined as the swelling degree. The results are shown in Table 2.

TABLE 2

|   | AN | Toluene | Pyridine | Acetic Anhydride | THF | DCM | Ethanol |
|---|---|---|---|---|---|---|---|
| A | 1.80 | 1.84 | 1.95 | 1.78 | 1.91 | 1.96 | 1.68 |
| B | 1.29 | 1.41 | 1.40 | 1.37 | 1.40 | 1.54 | 1.31 |
| C | 1.67 | 1.84 | 1.90 | 1.76 | 1.90 | 2.01 | 1.75 |
| D | 1.17 | 1.22 | 1.22 | 1.25 | 1.23 | 1.31 | 1.19 |
| E | 1.86 | 1.97 | 1.95 | 1.97 | 1.84 | 1.95 | 1.71 |
| F | 1.14 | 1.91 | 1.93 | 1.36 | 1.98 | 1.97 | 1.22 |

(Note)
AN stands for acetonitrile,
THF stands for tetrahydrofuran, and
DCM stands for dichloromethane.

As seen from Table 2, the swelling degree of the porous resin particle according to the present invention is from 1.68 to 1.96 in A, from 1.29 to 1.54 in B, from 1.67 to 2.01 in C, from 1.17 to 1.31 in D, and from 1.71 to 1.97 in E, whereas the swelling degree of porous resin particle F of Comparative Example is from 1.14 to 1.98. That is, the porous resin particle obtained by the method of the present invention does not greatly vary in the swelling degree among various organic solvents, and therefore when used as a support for solid phase synthesis, it provides a reaction site allowing a chemical reaction to proceed efficiently.

While the present invention has been described in detail and with reference to specific embodiments thereof, it will be apparent to one skilled in the art that various changes and modifications can be made therein without departing from the scope thereof.

This application is based on Japanese patent application No. 2007-286836 filed on Nov. 5, 2007, the entire contents thereof being hereby incorporated by reference.

Further, all references cited herein are incorporated in their entireties.

What is claimed is:

1. A method for producing a porous resin particle having a functional group X, the method comprising:
dissolving a radical polymerizable aromatic monovinyl monomer and a radical polymerizable aromatic divinyl monomer together with a polymerization initiator in an organic solvent to prepare a monomer solution;
dispersing the monomer solution in water in the presence of a dispersion stabilizer to obtain a suspension polymerization reaction mixture; and
performing a suspension copolymerization while adding, when 5 to 60% of the entire polymerization time of the suspension copolymerization is passed, a mercapto compound represented by the formula (I):

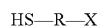  (I)

wherein R represents an alkylene group having a carbon number of 2 to 12, and the functional group X represents a functional group selected from a hydroxy group and a primary amino group, to the suspension polymerization reaction mixture.

2. The method for producing a porous resin particle having a functional group X according to claim 1, wherein the proportion of the aromatic divinyl monomer is 6 to 80 wt % based on the total amount of the aromatic monovinyl monomer and the aromatic divinyl monomer, and the mercapto compound is added to the suspension polymerization reaction mixture in an amount of 1 to 20 wt % based on the total amount of the aromatic monovinyl monomer and the aromatic divinyl monomer.

3. The method for producing a porous resin particle having a functional group X according to claim 1, wherein the aromatic monovinyl monomer is styrene.

* * * * *